(12) United States Patent
Moriyasu

(10) Patent No.: US 11,244,445 B2
(45) Date of Patent: Feb. 8, 2022

(54) MEDICAL INFORMATION PROCESSING APPARATUS

(71) Applicant: CANON MEDICAL SYSTEMS CORPORATION, Otawara (JP)

(72) Inventor: Kenta Moriyasu, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 214 days.

(21) Appl. No.: 16/576,048

(22) Filed: Sep. 19, 2019

(65) Prior Publication Data

US 2020/0098106 A1 Mar. 26, 2020

(30) Foreign Application Priority Data

Sep. 20, 2018 (JP) .............................. JP2018-175892

(51) Int. Cl.
*G06T 7/00* (2017.01)
*A61B 6/00* (2006.01)
*G16H 10/60* (2018.01)
*G06N 3/08* (2006.01)
*G06N 20/00* (2019.01)
*G16H 30/40* (2018.01)
*A61B 6/03* (2006.01)

(52) U.S. Cl.
CPC .......... *G06T 7/0012* (2013.01); *A61B 6/5217* (2013.01); *G06N 3/08* (2013.01); *G06N 20/00* (2019.01); *G16H 10/60* (2018.01); *G16H 30/40* (2018.01); *A61B 6/032* (2013.01); *G06T 2207/10081* (2013.01); *G06T 2207/30096* (2013.01)

(58) Field of Classification Search
CPC ......... G06T 7/0012; G06T 2207/10081; G06T 2207/30096; G06T 2207/10116; G06T 2207/20081; G06T 2207/20084; G06T 2207/30168; G06T 2207/10072; A61B 6/5217; A61B 6/032; A61B 6/542; G16H 10/60; G16H 30/40; G16H 50/70; G06N 3/08; G06N 20/00; G06N 3/0454; G06N 3/0472; G06N 20/10
See application file for complete search history.

(56) References Cited

U.S. PATENT DOCUMENTS

| 9,226,727 | B2 | 1/2016 | Coussios et al. | |
|---|---|---|---|---|
| 2010/0177950 | A1* | 7/2010 | Donovan | G16H 50/30 382/133 |
| 2013/0018232 | A1* | 1/2013 | D'Souza | A61N 5/1049 600/300 |
| 2014/0348401 | A1* | 11/2014 | Xu | A61B 6/545 382/128 |

(Continued)

*Primary Examiner* — Kim Y Vu
*Assistant Examiner* — Molly Delaney
(74) *Attorney, Agent, or Firm* — Oblon, McClelland, Maier & Neustadt, L.L.P.

(57) ABSTRACT

According to one embodiment, a medical information processing apparatus includes processing circuitry. The processing circuitry is configured to acquire information on an accuracy of a trained model that outputs information on a lesion included in data related to a medical image based on inputted data related to the medical image. Further, the processing circuitry is configured to determine a data collection condition for the medical image in a medical image diagnostic apparatus based on the information on the accuracy.

11 Claims, 13 Drawing Sheets

(56) References Cited

U.S. PATENT DOCUMENTS

| | | | | |
|---|---|---|---|---|
| 2016/0364862 A1* | 12/2016 | Reicher | .................... | G06K 9/66 |
| 2018/0043182 A1* | 2/2018 | Wu | ........................ | G16H 70/20 |
| 2018/0204325 A1* | 7/2018 | Steigauf | ................ | G06T 7/0014 |
| 2018/0247714 A1* | 8/2018 | Lee | .................... | A61B 5/02055 |
| 2018/0286518 A1* | 10/2018 | Raju | ....................... | G16H 50/30 |
| 2018/0341752 A1* | 11/2018 | Bernard | ................. | G16H 30/20 |
| 2019/0050987 A1* | 2/2019 | Hsieh | ..................... | G16H 30/40 |
| 2019/0143145 A1* | 5/2019 | Laurence, Jr. | ......... | A61B 34/10 |
| | | | | 600/1 |
| 2019/0147588 A1* | 5/2019 | Rowley Grant | ........ | G06T 5/002 |
| | | | | 382/131 |
| 2019/0333623 A1* | 10/2019 | Hibbard | ............... | A61N 5/1031 |

\* cited by examiner

MEDICAL INFORMATION PROCESSING APPARATUS

CROSS-REFERENCE TO RELATED APPLICATIONS

This application claims the benefit of priority of Japanese Patent Application No. 2018-175892, filed Sep. 20, 2018, the entire contents of which are incorporated herein by reference.

FIELD

Embodiments described herein relate generally to a medical information processing apparatus.

BACKGROUND

The medical image of the object generated by the medical image diagnostic apparatus has higher image quality as the imaging time is increased, whereby a diagnostic accuracy is improved. Examples of the medical image diagnostic apparatus include a nuclear medical diagnostic apparatus, an X-ray CT (Computed Tomography) apparatus, a magnetic resonance imaging (MRI) apparatus, an X-ray diagnostic apparatus, and an ultrasonic diagnostic apparatus.

Meanwhile, when the imaging time becomes longer, the burden on the object to be imaged becomes larger. In particular, in the medical diagnostic imaging apparatus that uses radiation, the exposure amount of the object increases as the imaging time increases.

In recent years, machine learning models have been variously developed that generate feature values in medical images, medical image data, or raw data thereof (hereinafter collectively referred to as data related to medical images) based on the data related to medical images.
Among parameters relating to medical images, some parameters such as noise affect the accuracy of feature quantities generated by a machine learning model. Among parameters related to medical images, some parameters such as noise affect the accuracy of feature values generated by the machine learning model. The values of these parameters that affect the accuracy of the feature value generated by the machine learning model are considered to change according to imaging conditions such as imaging time in the medical image diagnostic apparatus.

DETAILED DESCRIPTION

Hereinbelow, a description will be given of a medical information processing apparatus according to embodiments of the present invention with reference to the drawings.

The medical information processing apparatus according to an embodiment adaptively determines the imaging condition of the medical image diagnostic apparatus according to the accuracy desired by the user of the feature value generated by the machine learning model. As the medical image diagnostic apparatus, various apparatuses such as a nuclear medical diagnostic apparatus, an X-ray CT apparatus, and an MRI apparatus can be used.

In general, according to one embodiment, a medical information processing apparatus includes processing circuitry. The processing circuitry is configured to acquire information on an accuracy of a trained model that outputs information on a lesion included in data related to a medical image based on inputted data related to the medical image. Further, the processing circuitry is configured to determine a data collection condition for the medical image in a medical image diagnostic apparatus based on the information on the accuracy.

First Embodiment

Figure 1:
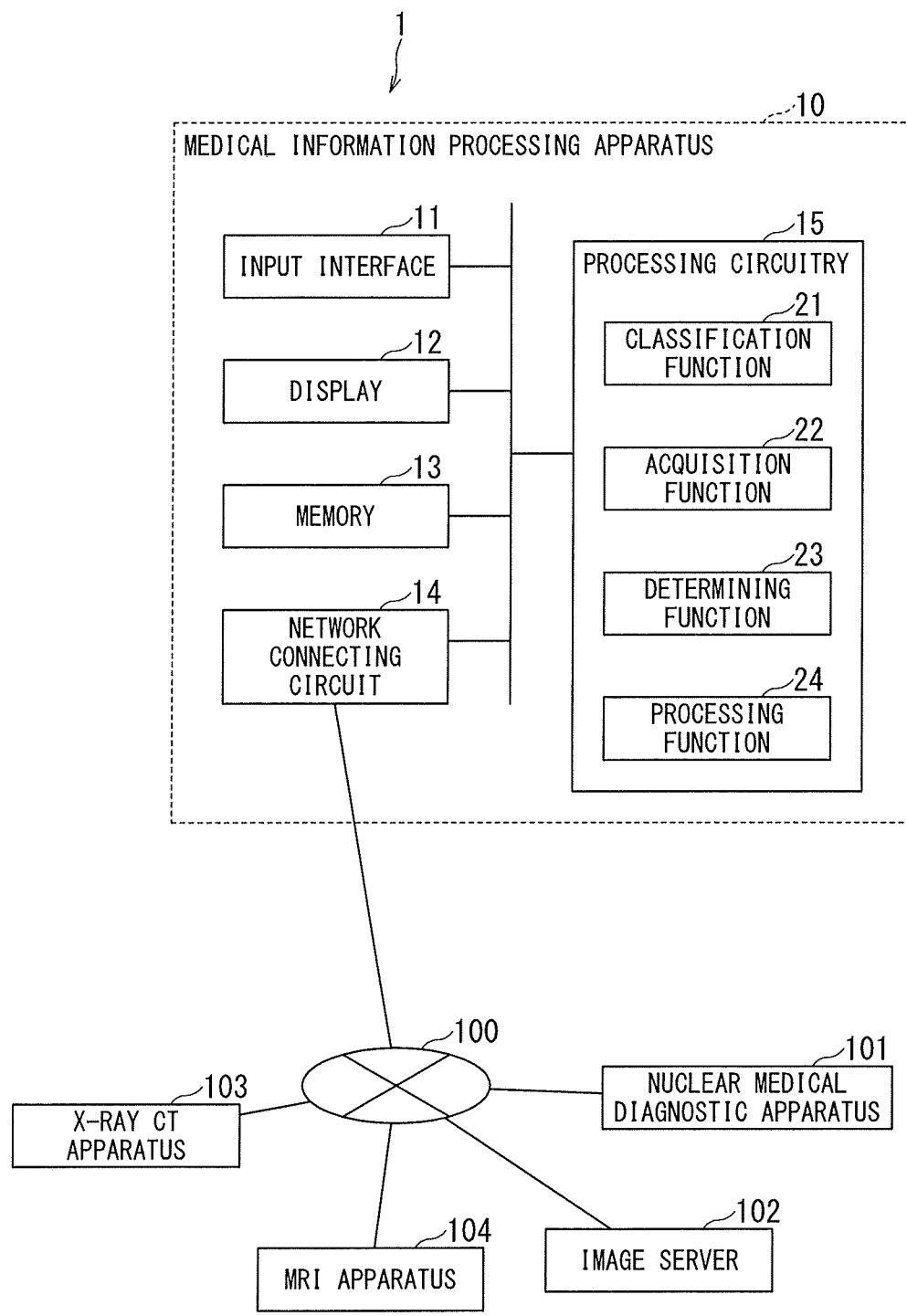
FIG. 1 is a block diagram showing an example of a medical information processing system including a medical information processing apparatus according to the first embodiment.

FIG. 1 is a block diagram showing an example of the medical information processing system 1 including the medical information processing apparatus 10 according to the first embodiment. The medical information processing apparatus 10 according to the first embodiment uses a single existing trained model. The medical information processing system 1 includes the medical information processing apparatus 10, medical image diagnosis apparatuses 101, 103, and 104 and an image server 102 connected to the medical information processing apparatus 10 via a network 100. The medical information processing system 1 may further include an information processing apparatus that realizes the single existing trained model.

The medical information processing apparatus 10 includes an input interface 11, a display 12, a memory 13, a network connecting circuit 14, and processing circuitry 15.

The input interface 11 is configured by a general input device such as a trackball, a switch button, a mouse, a keyboard, or a ten key, and outputs an operation input signal corresponding to a user operation to the processing circuitry 15. The display 12 displays various kinds of information. For example, the display 12 is configured by a general display device such as a liquid crystal display and an OLED (Organic Light Emitting Diode) display.

The memory 13 has a configuration including a processor-readable recording medium such as a semiconductor memory element, e.g., a RAM (Random Access Memory) or a flash memory, a hard disk, an optical disk, and the like. The memory 13 stores programs, parameter data, and other data used by the processing circuitry 15. A part or all of the programs and data in the recording medium of the memory 13 may be downloaded by communication via the network 100, or may be stored to the memory 13 via a portable storage medium such as an optical disk.

The network connecting circuit 14 implements various information communication protocols according to the network 100. The network connecting circuit 14 connects the medical information processing apparatus 10 and other devices in accordance with these various protocols via the network 100. The network refers to a general information communication network using telecommunications technology and includes not only a wireless/wired LAN such as a hospital backbone local area network (LAN) and the Internet network, but also a telephone communication network, an optical fiber communication network, a cable communication network, a satellite communication network, and other networks.

The medical information processing apparatus 10 is connected to the nuclear medical diagnostic apparatus 101 and the image server 102 via the network 100 such that data can be transmitted and received between them. The medical information processing apparatus 10 may be connected to the X-ray CT apparatus 103 and the MRI apparatus 104 via the network 100 such that data can be transmitted and received between them.

The processing circuitry 15 implements a function for performing overall control of the medical information processing apparatus 10. Further, the processing circuitry 15 is a processor configured to execute, by reading out and executing the imaging condition determination program stored in the memory 13, a procedure for determining the imaging condition of the medical image diagnostic apparatus according to the accuracy desired by the user for the feature value generated by the machine learning model.

As shown in FIG. 1, the processor of the processing circuitry 15 implements the classification function 21, the acquisition function 22, and the determining function 23. Further, the processor of the processing circuitry 15 may further implement the processing function 24. Each of these functions is stored in the memory 13 in the form of a program.

The classification function 21 acquires data groups obtained by classifying the data related to the medical images (medical image, medical image data, or raw data) into a plurality of groups according to parameter values related to the accuracy of the trained model. The classification function 21 calculates the accuracy of the trained model for each of the classified data groups. The raw data is data before image reconstruction, and for example, sinogram data can be used as the raw data. The classification function 21 is an example of an arrangement unit.

The trained model outputs information related to the feature value in the data related to the medical image based on the input of the data related to the medical image. The information on the feature value in the data related to the medical image is information on the lesion in the medical image, for example.

Specifically, the trained model may extract at least one lesion in a medical image based on input of the data related to the medical image. For example, the trained model extracts a lesion by outputting information on lesions (for example, the presence or absence of lesions), more specifically, by outputting information on the position of the lesion.

In this case, the parameter value related to the accuracy of the trained model includes the size of the lesion to be extracted. It is considered that the larger the size of the lesion to be extracted, the easier the extraction of the lesion and the higher the lesion extraction accuracy.

The parameter value related to the accuracy of the trained model includes information on the image quality. The information on the image quality includes, for example, a parameter value (image quality index) related to the image quality. It is considered that the higher the quality of the medical image, the higher the accuracy of the lesion extraction. Further, the data related to the medical image may be classified by further using the body part as the parameter value related to the accuracy of the trained model.

When the medical image diagnostic apparatus is the nuclear medical diagnostic apparatus 101 and the medical image is a nuclear medicine image, the noise of the liver, the contrast of the accumulation portion of a predetermined size such as the 10 mm accumulation portion, the contrast to noise ratio, and the like, can be used as the parameter value (image quality index) related to the image quality.

The nuclear medical diagnostic apparatus 101 uses the property that a medicine (blood flow marker, tracer) containing a radioisotope (hereinafter referred to as RI) is selectively taken into a specific tissue or organ in the living body, and detects Gamma rays emitted from the distributed RI in the living body by a gamma ray detector disposed outside the living body. It is known that the image of the liver portion in a nuclear medicine image is more sensitive to the amount of noise than other body parts, and becomes flat image when the noise is low, and becomes coarse image when the noise is high.

When the noise in the liver portion is large, the amount of signal is insufficient due to low concentration of medicine or short collection time. When the noise in the liver portion is small, the amount of signal is considered to be sufficient. In this case, the correct rate (accuracy) of the lesion extraction by the trained model (for example, the accuracy of information on the position of the lesion outputted by the trained model) is expected to be high.

For example, when the liver noise is used as the parameter value related to the image quality, the medical images each including at least the liver are classified into, for example, noise of large, medium and small according to the noise of the liver. Body parts such as the head other than the liver included in the same medical image as the liver are classified according to the noise of the liver. That is, the noise level (for example, large, medium, and small) of a body part included in the medical image is represented by the noise of the liver. The noise level of body parts may be represented by the noise of the spine or the noise of the muscle instead of the noise of the liver.

In the following description, basically, the medical image diagnostic apparatus is the nuclear medical diagnostic apparatus 101, the medical image is the nuclear medicine image, and the parameter values related to the accuracy of the trained model include the lesion size and the parameter values related to the image quality of the medical image.

In the above example, the classification function 21 acquires data groups obtained by classifying the data related to the medical images into the plurality of groups according to the lesion size in the medical image and the parameter value related to the image quality of the medical image. Further, the classification function 21 calculates the accuracy of the trained model for each of these classified data groups. As a result, it is possible to correlate the lesion size, the parameter value related to the image quality, and the accuracy of the trained model.

The acquisition function 22 acquires a set value of the size of the lesion received from the user via the input interface 11 and a desired value of the accuracy of the trained model. Further, the acquisition function 22 acquires the data related to the medical image (medical image, medical image data, or raw data) obtained by imaging the object by the medical image diagnostic apparatus. For example, the acquisition function 22 acquires the data related to the nuclear medicine image from the nuclear medical diagnostic apparatus 101 or the image server 102.

Further, the acquisition function 22 may acquire information on the image quality of the interest target region of the nuclear medicine image data based on the input of the data related to the nuclear medicine image being currently collected in the nuclear medical diagnostic apparatus 101.

The determining function 23 determines the imaging conditions of the medical image diagnostic apparatus based on information on the accuracy of the trained model. In the above example, the information on the accuracy of the trained model includes information on the lesion extraction accuracy (correct answer rate) of the trained model. In the above example, the determining function 23 automatically determines at least the data collection time among the data collection conditions related to the nuclear medicine image in the nuclear medical diagnostic apparatus 101 as the imaging condition.

Specifically, in the above example, based on the relationship between the data collection time and the parameter value related to the image quality, the accuracy of the trained model obtained for each data group, the set value of the lesion size, and the trained model, the determining function 23 automatically determines the data collection time. The classification function 21 associates the lesion size, the parameter value related to the image quality, and the accuracy of the trained model. With the association, when the set value of the lesion size and the desired value of the accuracy of the trained model are acquired, the parameter value related to the image quality associated with these values is determined. Therefore, when the relationship between the parameter value related to the image quality and the data collection time is known, the data collection time corresponding to these values can be determined.

In addition, when the acquisition function 22 acquires information on the image quality of the interest target region based on the inputted data related to the nuclear medicine image being currently collected. The determining function 23 may determine the collection time of the data related to the nuclear medicine image in the nuclear medical diagnostic apparatus 101 being currently collected based on the information related to the image quality of the interest target region.

When the medical image diagnostic apparatus is the X-ray CT apparatus 103, the acquisition function 22 acquires data related to the X-ray CT image from the X-ray CT apparatus 103 or the image server 102. Further, the determining function 23 may determine the X-ray dose or the rotation speed of the X-ray tube of the X-ray CT apparatus 103 as the imaging condition, based on information on the accuracy of the trained model. This is because the image quality of the X-ray CT image is generally considered to change according to the amount of tube current mAs applied to the X-ray tube.

Further, when the medical image diagnostic apparatus is the MRI apparatus 104, the acquisition function 22 acquires data related to the MRI image from the MRI apparatus 104 or the image server 102. Generally, the image quality of the MRI image is considered to change according to the thinning rate and/or the number of additions. Therefore, the determining function 23 may determine the thinning rate and/or the number of additions of the MRI apparatus 104 as the imaging conditions based on information on the accuracy of the trained model.

Further, when the medical information processing apparatus 10 implements the processing function 24, the processing function 24 outputs the feature value in the data related to the medical image based on the input of the data related to the medical image of the object which is imaged by the medical image diagnostic apparatus according to the imaging conditions determined by the determining function 23. Machine learning technique is used for this processing. As the machine learning, the machine learning using SVM (support vector machine) may be used, or deep learning using the multi-layer neural networks such as CNN (convolutional neural network) and convolutional deep belief network (CDBN) may be used, for example. In some embodiments, the process is performed, for example, using the machine learning as disclosed in Christopher M. Bishop (2006) "Pattern recognition and machine learning," Springer, pp. 225-290, which is incorporated herein by reference.

In the following, an example is shown in which the processing function 24 includes the neural network 31, and a lesion extraction result is generated based on the data related to the medical image by using deep learning technique.

For example, the processing function 24 extracts a lesion from the nuclear medicine image data based on the nuclear medicine image data of the object imaged during the collection time determined by the determining function 23.

Subsequently, the operation of the processing circuitry 15 according to the present embodiment will be described.

Figure 2:
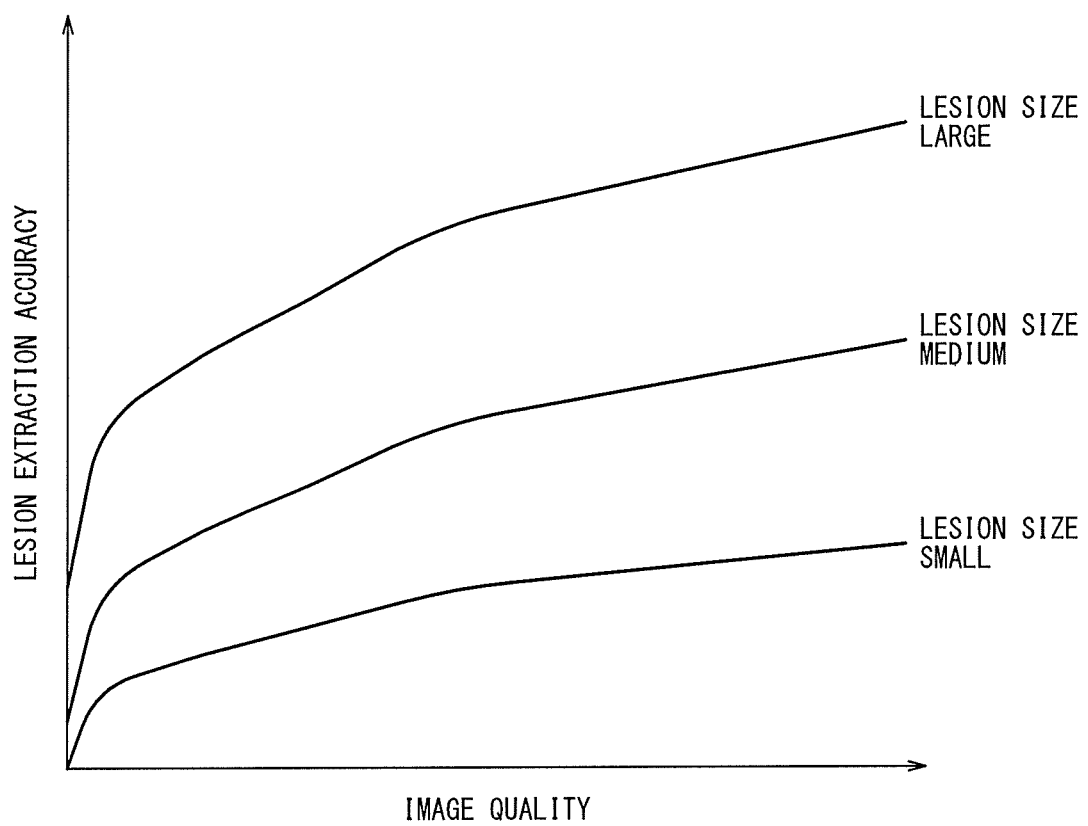
FIG. 2 is an explanatory diagram showing an example of a relationship between an image quality of a medical image, a size of a lesion included in the medical image, and a lesion extraction accuracy of a trained model.

FIG. 2 is an explanatory diagram showing an example of the relationship between the image quality of the medical image, the size of the lesion included in the medical image, and the lesion extraction accuracy of the trained model.

The medical information processing apparatus 10 according to the first embodiment uses a single existing trained model. This existing trained model is generated using a medical image (training data) input at the time of training without distinction of lesion size and image quality. However, when a medical image is input to this trained model, the accuracy of lesion extraction (lesion extraction correct answer rate) increases as the lesion size increases and as the image quality of the medical image increases (see FIG. 2).

Therefore, the classification function 21 according to the first embodiment classifies the validation data into a plurality of data groups according to the parameter values related to the image quality and the lesion size, and calculates in advance a lesion extraction accuracy for each classified group.

Figure 3:
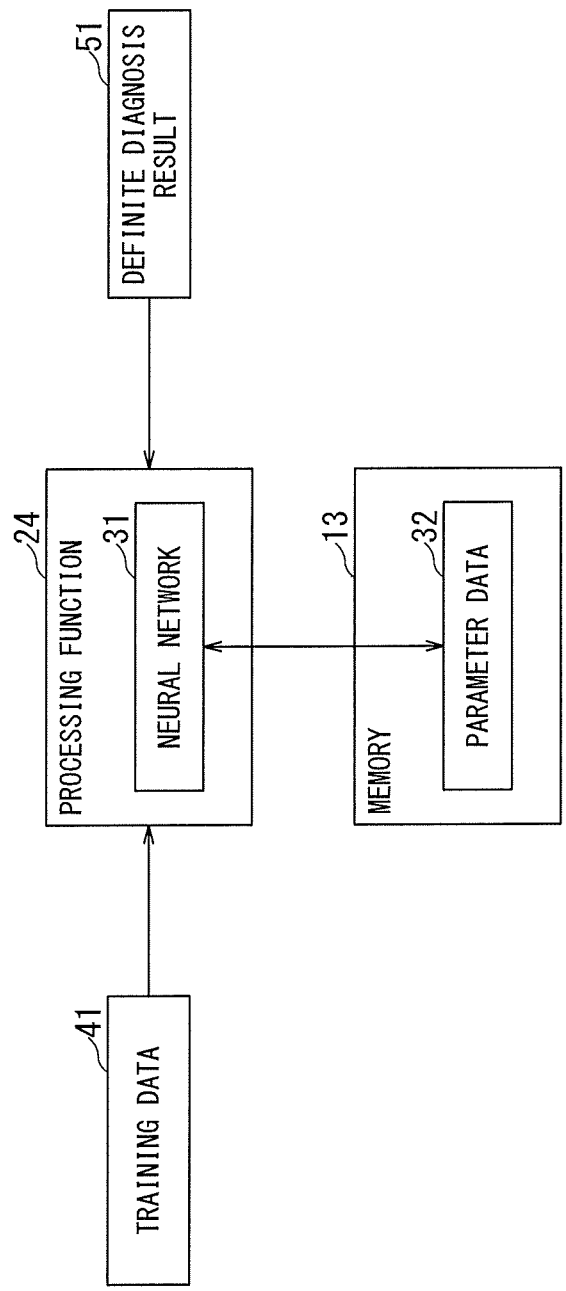
FIG. 3 is an explanatory diagram showing an example of a data flow at the time of training a processing function.

FIG. 3 is an explanatory diagram showing an example of a data flow at the time of training the processing function 24.

The processing function 24 sequentially updates the parameter data 32 by inputting a large number of training data 41 and performing training. The training data 41 is the data related to the medical image prepared without distinction of the lesion size and the image quality. The ideal lesion extraction result 51 is preferably a definite diagnosis result determined by taking out a tissue from the imaging object and making a diagnosis.

Each time the training data 41 is input, the processing function 24 updates the parameter data 32 such that the result of processing the data related to the medical image by the neural network 31 approaches the definite diagnosis result 51 of lesion extraction. In general, when the change rate of the parameter data 32 converges within a threshold value, it is determined that training is finished. Hereinafter, the parameter data 32 after the training is particularly referred to as the trained parameter data 32a.

Note that the type of training input data and the type of input data during operation shown in FIG. 3 should match each other. For example, when the data related to the medical image as input data during operation is raw data, the training data 41 during training should be raw data.

As a result of the training shown in FIG. 3, the neural network 31 and the trained parameter data 32a constitute a trained model 30. The trained model 30 may be constructed by an integrated circuit such as an application specific integrated circuit (ASIC) or a field programmable gate array (FPGA).

In the first embodiment, the neural network 31 is stored in the memory 13 or a storage medium connected to the medical information processing apparatus 10 via the network 100 in the form of a program. The trained parameter data 32a may be stored in the memory 13 or may be stored in a storage medium connected to the medical information processing apparatus 10 via the network 100. When the neural network 31 is stored in a storage medium connected to the medical information processing apparatus 10 via the network 100, the medical information processing apparatus 10 may not include the processing function 24. In this case, a function corresponding to the processing function 24 is implemented by an information processing apparatus including a processor that can use the neural network 31 stored in the storage medium, and input data is given from the medical information processing apparatus 10 to the function, and then the medical information processing apparatus 10 may receive a lesion extraction result from the function of the information processing apparatus.

Figure 4:
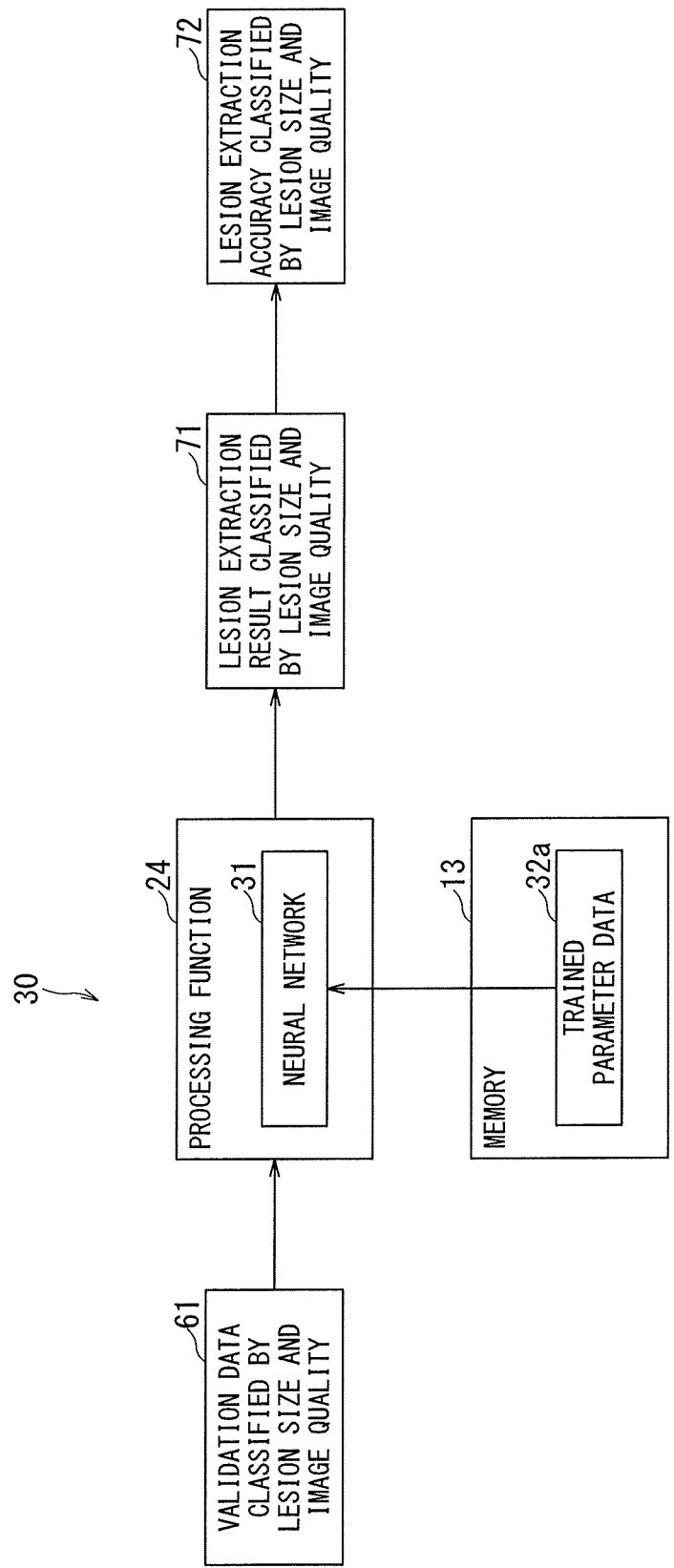
FIG. 4 is a diagram for explaining an example of the operation of a classification function before operation of a trained model.
Figure 5:
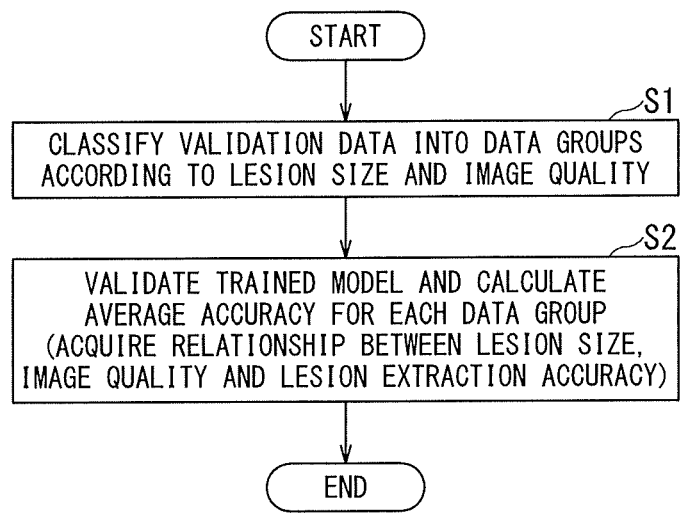
FIG. 5 is a flowchart showing an example of a procedure for obtaining an accuracy of each lesion extraction result of a plurality of data groups by a classification function before the operation of the trained model according to the first embodiment.

FIG. 4 is a diagram for explaining an example of the operation of the classification function 21 before operation of the trained model 30. FIG. 5 is a flowchart showing an example of a procedure for obtaining the accuracy 72 of each lesion extraction result 71 of a plurality of data groups 61 by the classification function 21 before the operation of the trained model 30 according to the first embodiment. In FIG. 5, reference numerals with numbers added to S indicate steps in the flowchart.

The classification function 21 classifies the validation data into a plurality of data groups 61 according to the size of the lesion and the parameter values related to the image quality of the lesion before the operation of the trained model 30 (step S1 in FIG. 5). This classification may be performed automatically or in response to a user input.

Then, the classification function 21 obtains the accuracy (correct answer rate) 72 of each lesion extraction result 71 of each of the classified data groups 61. As a result, the lesion size, the parameter value related to the image quality, and the lesion extraction accuracy of the trained model 30 can be associated (step S2 in FIG. 5).

Figure 6:
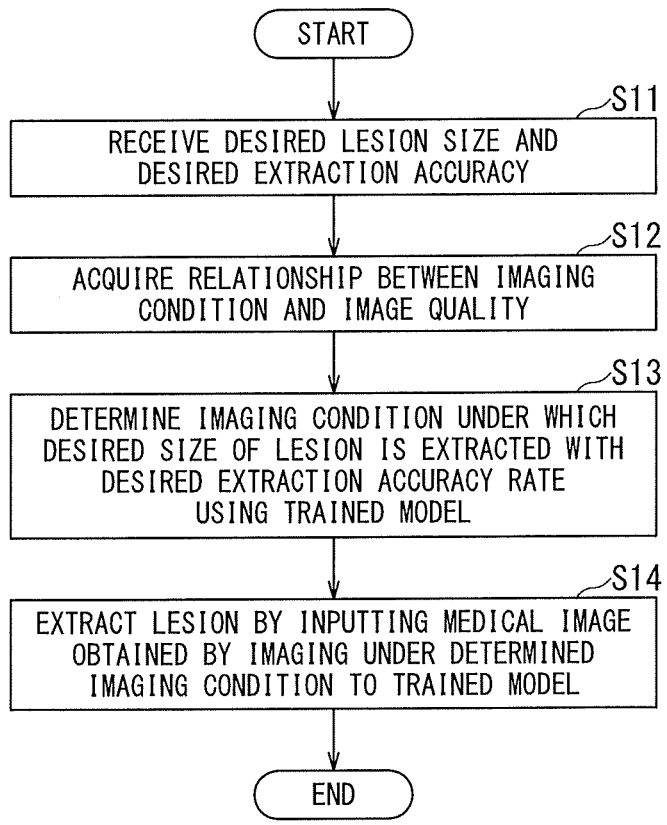
FIG. 6 is a flowchart showing an example of a procedure during the operation of the trained model according to the first embodiment.

FIG. 6 is a flowchart showing an example of a procedure during the operation of the trained model 30 according to the first embodiment. In FIG. 6, reference numerals with numbers added to S indicate steps in the flowchart.

At the time of operation of the trained model 30, the acquisition function 22 first obtains a set value of the size of the lesion and a desired value of the correct rate (accuracy) of lesion extraction of the trained model 30 received from the user via the input interface 11 (step S11). In the case where there is a lesion existing in the same part of the same object confirmed in advance by the X-ray CT image or the like, the set value of the lesion size may be automatically set using the size of the lesion confirmed in advance, or may be automatically set to a smaller size (for example, the smallest settable size) when it should be observed firmly, e.g., at a medical examination.

In step S2 of FIG. 5, the lesion size, the parameter value related to the image quality, and the lesion extraction accuracy of the trained model 30 are already associated with each other. Hence, when the set value of the lesion size and the desired value of the correct rate of lesion extraction are acquired in step S11, the parameter values related to the image quality associated with these values are determined.

Next, the determining function 23 acquires the relationship between the data collection time as the imaging condition and the parameter value related to the image quality (step S12). Even if the noise level of the medical image represented by the noise of the liver part is set as the parameter value related to the image quality, it is only necessary to have a medical image including the lesion extraction target during the operation of the trained model 30, and a medical image of the liver is not necessary during the operation of the trained model.

The relationship between the imaging condition and the parameter value related to the image quality may be set in advance or may be obtained in real time during the collection of medical images. A specific example of a method for obtaining the relationship between the imaging condition and the parameter value related to the image quality will be described later with reference to FIGS. 11-15.

Next, in step S13, the determining function 23 determines imaging conditions under which the desired lesion size is extracted with the desired extraction correct answer rate by the trained model 30. Specifically, as a result of step S11, parameter values related to the image quality necessary to obtain the desired lesion extraction correct answer rate with the desired lesion size are already acquired. Thus, when the data collection time as the imaging conditions and the parameter value related to the image quality are acquired in step S12, the determining function 23 can automatically determine the data collection time necessary for acquiring the parameter value.

When the medical information processing apparatus 10 implements the processing function 24, the processing function 24 inputs the data related to the medical image obtained by imaging the object using the imaging conditions determined by the determining function 23 to the trained model 30, thereby extracting the lesion from the data related to the medical image (step S14). The collection time is a time determined according to the set value of the lesion size and the desired value of the correct rate (accuracy) of lesion extraction of the trained model 30. Therefore, the accuracy of the lesion extraction by the processing function 24 for the nuclear medicine image data of the object imaged during the determined data collection time, for the lesion having a size equal to or larger than the set value acquired by the acquisition function 22, is higher than the desired value acquired by the acquisition function 22.

The medical information processing system 1 including the medical information processing apparatus 10 according to the first embodiment can adaptively determine the imaging conditions by using the single existing trained model 30, according to the desired lesion size and the desired lesion extraction accuracy. Hence, in a PET-CT apparatus for example, the data collection time that is more suitable for the trained model 30 than when the technician manually determines the data collection time based on drag dosage, weight or height of the object, and the like, can be automatically set.

Second Embodiment

Next, a second embodiment of the medical information processing system 1 including the medical information processing apparatus 10 will be described. The medical information processing apparatus 10 according to the second embodiment is different from the medical information processing apparatus 10 according to the first embodiment in that, a processing function 24 is essential, and a plurality of trained models are generated and used by the processing function 24 according to parameter values related to the accuracies of the trained models.

Figure 7:
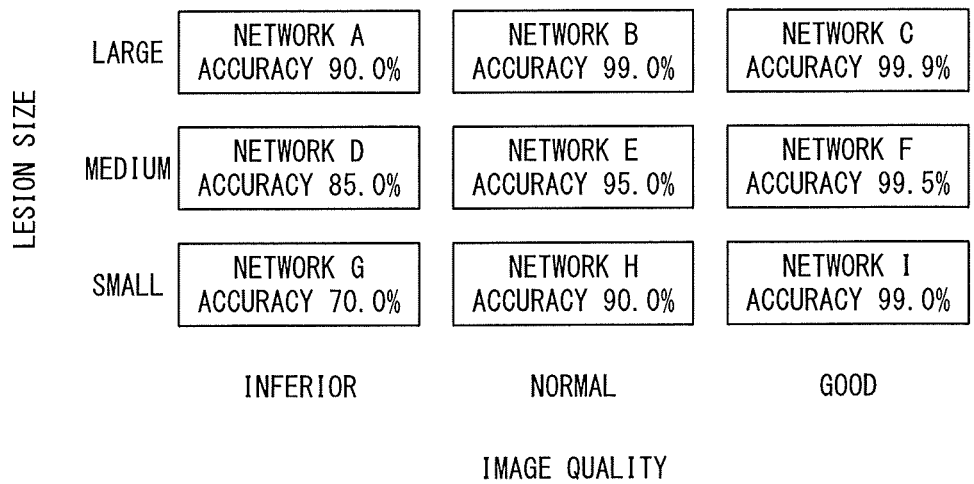
FIG. 7 is an explanatory diagram showing an example of a plurality of trained models according to the second embodiment.
Figure 8:
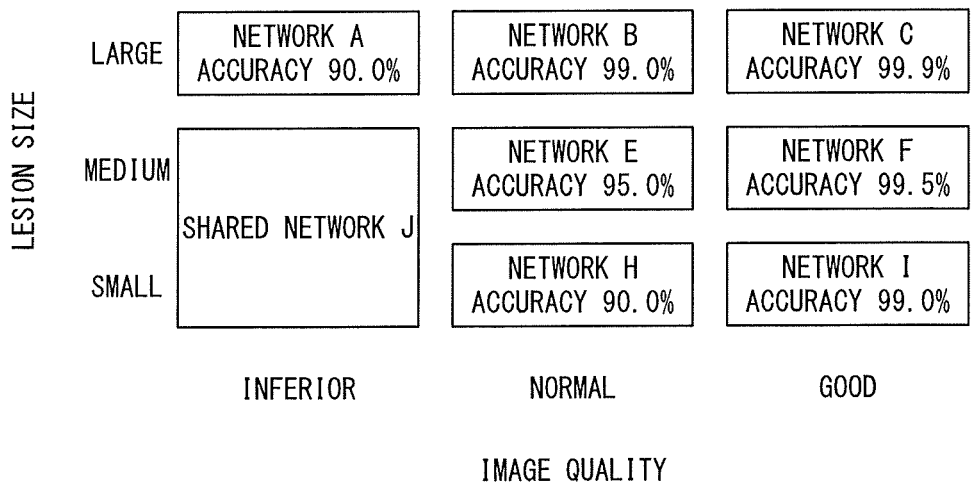
FIG. 8 is an explanatory diagram showing a variation of the plurality of trained models according to the second embodiment.

FIG. 7 is an explanatory diagram showing an example of a plurality of trained models according to the second embodiment. FIG. 8 is an explanatory diagram showing a variation of the plurality of trained models according to the second embodiment.

Figure 9:
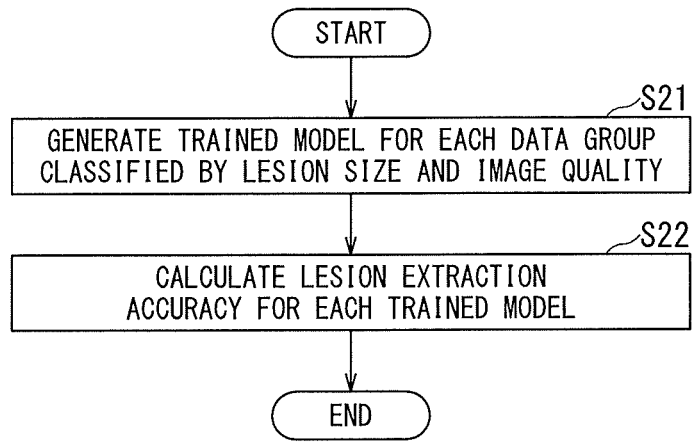
FIG. 9 is a flowchart showing an example of a procedure for generating the plurality of trained models according to parameter values related to the accuracy of the trained model by a processing function according to the second embodiment.

Further, FIG. 9 is a flowchart showing an example of a procedure for generating the plurality of trained models according to parameter values related to the accuracy of the trained model by the processing function 24 according to the second embodiment. In FIG. 9, reference numerals with numbers added to S indicate steps in the flowchart.

The classification function 21 according to the second embodiment classifies a large number of pieces of data related to medical images into a plurality of groups according to parameter values related to the accuracy of the trained model. In FIG. 7, an example of classifying data is given in which the lesion size and the parameter values related to the image quality are used as the parameter values related to the accuracy of the trained model, and three classifications are set according to the size of the lesion and three classifications are set according to the parameter value related to the image quality.

The processing function 24 according to the second embodiment generates the trained model 30A-30I (see Network A-I in FIGS. 7 and 8) for each classified input data group (step S21 in FIG. 9).

The classification function 21 according to the second embodiment calculates the correct answer rate (see "accuracy" in FIGS. 7 and 8) for each trained model 30A-30I (step S22 in FIG. 9).

It should be noted that conditions that do not need to be classified finely may be generated together in one trained model (see shared Network J in FIG. 8). In this case, as in the first embodiment, the validation data may be classified prior to the operation according to the medium size (corresponding to Network D in FIG. 7) and small size (corresponding to Network G in FIG. 7) of the lesion with respect to this one shared trained model 30J, and the accuracy of the shared trained model 30J may be obtained for each classified group.

According to the above procedure, the trained models 30A-30I can be generated according to the parameter values related to the accuracy of the trained model.

Figure 10:
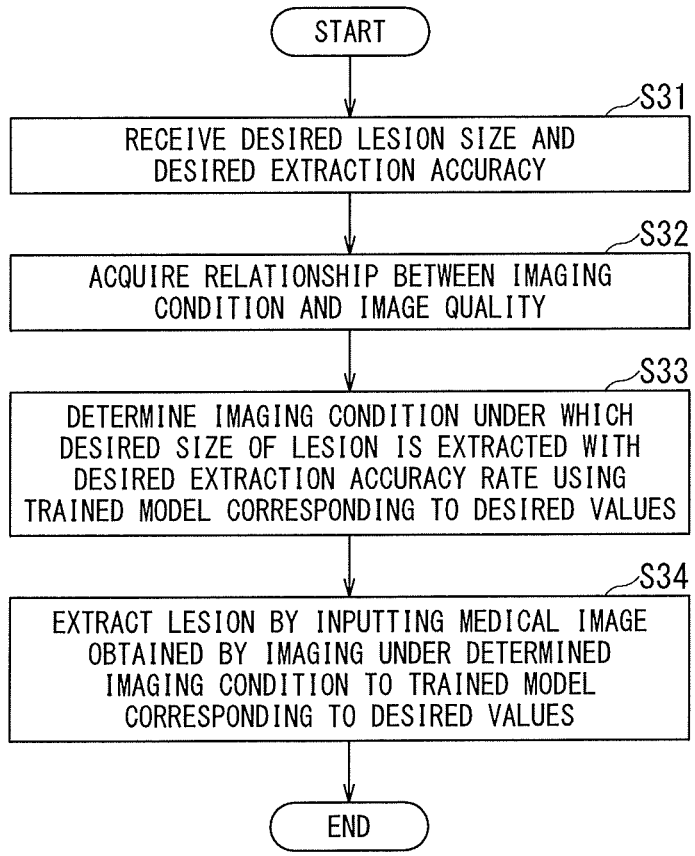
FIG. 10 is a flowchart showing an example of a procedure when operating the plurality of trained models according to the second embodiment.

FIG. 10 is a flowchart showing an example of a procedure when operating the plurality of trained models 30A-30I according to the second embodiment. In FIG. 10, reference numerals with numbers added to S indicate steps in the flowchart.

In the operation of the trained model 30A-30I in the second embodiment, as in the first embodiment, the acquisition function 22 obtains a set value of the size of the lesion and a desired value of the correct rate (accuracy) of lesion extraction of the trained model 30 received from the user via the input interface 11 (step S31).

Next, as in the first embodiment, the determining function 23 acquires the relationship between the data collection time as the imaging condition and the parameter value related to the image quality (for example, the noise level of the medical image represented by the noise of the liver) (step S32).

Next, in step S33, the determining function 23 determines the imaging conditions under which the desired lesion size is extracted with the desired extraction accuracy by the trained model, among the plurality of trained models 30A-30I, corresponding to the lesion size and the extraction accuracy acquired in step S31.

In step S34, the processing function 24 inputs data related to the medical image obtained by imaging the object using the imaging conditions determined by the determining function 23 into one trained model corresponding to the lesion size and the extraction accuracy acquired in step S31, thereby extracting the lesion from the data related to the medical image (step S34).

According to the medical information processing system 1 including the medical information processing apparatus 10 according to the second embodiment, a plurality of trained models 30A-30I can be generated according to parameter values related to the accuracy of the trained model, and it is possible to adaptively determine the imaging condition of the medical image using one corresponding trained model according to the desired lesion size and the desired lesion extraction correct answer rate.

Next, a specific example of the relationship between the imaging conditions and parameter values related to the image quality will be described. In the following description, an example is shown in which the imaging condition is the data collection time in the nuclear medical diagnostic apparatus 101.

Figure 11:
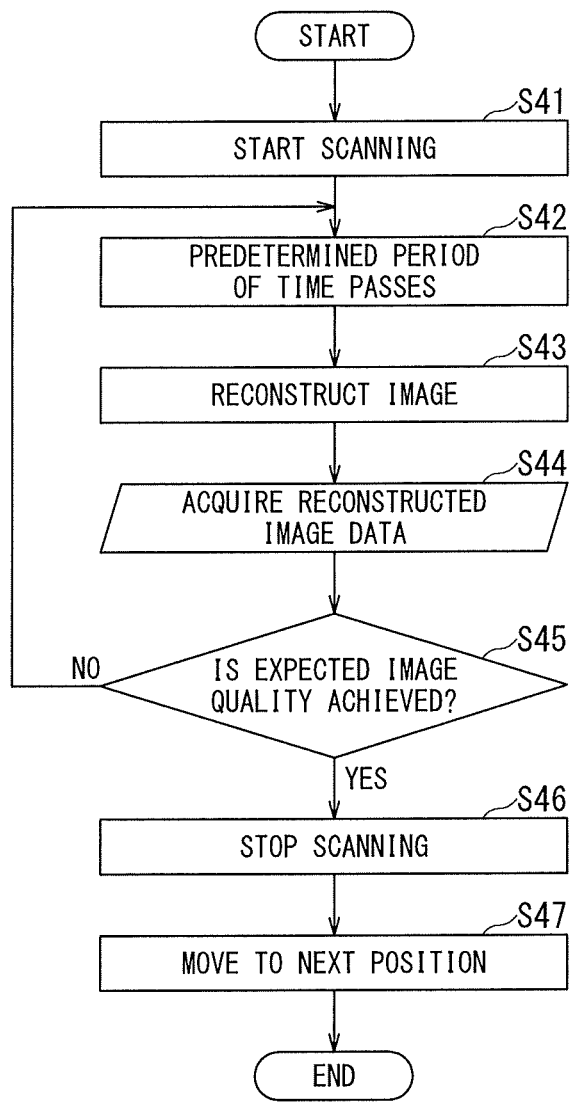
FIG. 11 is a flowchart showing an example of a procedure for obtaining a relationship between a collection time and a parameter value related to image quality based on medical image data reconstructed in real time during imaging.

FIG. 11 is a flowchart showing an example of a procedure for obtaining a relationship between a collection time and a parameter value related to image quality based on medical image data reconstructed in real time during imaging. The procedure shown in FIG. 11 is performed concurrently with steps S12 and S13 in FIG. 6 or steps S32 and S33 in FIG. 10.

In the nuclear medical diagnostic apparatus 101, scanning is started (step S41), and when a predetermined period of time has passed (step S42), image reconstruction is executed in real time from raw data up to that timing, and the medical image data is generated (step S43).

The acquisition function 22 acquires the reconstructed medical image data (step S44). Then, the determining function 23 calculates the parameter value related to the image quality of the reconstructed medical image data, and determines whether the parameter value related to the image quality necessary for obtaining the desired lesion extraction correct answer rate with the desired lesion size has been reached (Step S45).

When the parameter value related to the image quality necessary for obtaining the desired lesion extraction correct answer rate with the desired lesion size is reached (YES in step S45), the determining function 23 determines the data collection time automatically by terminating scanning (raw data collection) in the nuclear medical diagnostic apparatus 101 (step S46). Then, the nuclear medical diagnostic apparatus 101 moves the object to the next imaging position, for example (step S47). Meanwhile, when the parameter value related to the image quality necessary for obtaining the desired lesion extraction correct answer rate with the desired lesion size has not been reached (NO in step S45), the process returns to step S42.

According to the above procedure, the data collection time can be automatically determined by directly calculating the parameter value related to the image quality of the medical image data reconstructed in real time during imaging.

Next, the first the second variations of the procedure shown in FIG. 11 will be described. In these variation examples, the determining function 23 calculates the parameter value related to the image quality of the interest target region of the medical image data reconstructed from the raw data in real time in step S45. Then, the determining function 23 automatically determines the data collection time by causing the nuclear medical diagnostic apparatus 101 to terminate the scan (raw data collection) based on the parameter value. In these variations, generally speaking, the determining function 23 causes the nuclear medical diagnostic apparatus 101 to terminate scanning (raw data collection) when the image quality of the interest target region is good, while the determining function 23 causes the nuclear medical diagnostic apparatus 101 to continue scanning (raw data collection) when the image quality of the interest target region is inferior.

The first variation of the procedure shown in FIG. 11, for example, is applied when performing so-called step-and-shoot method, in which repetitive imaging is performed such that, after performing the raw data collection of the interest target region, the raw data collection of the next interest target region is performed by moving the top plate on which the object is placed. In this case, the raw data collection is performed for each interest target region such as the head, chest, abdomen, and legs.

In the first variation of the procedure shown in FIG. 11, a trained model that outputs whether the image quality of the medical image satisfies a predetermined condition based on the inputted medical image is constructed in advance for each interest target region. The predetermined condition is a classification condition of good or inferior image quality, and is determined by a user who prepares training data of the model. For example, the user may prepare training data by using a medical image having an image quality sufficient for interpretation and diagnosis of the interest target region as a good label and a medical image having an insufficient image quality as an inferior label. The user may also prepare training data with the medical images such that the medical image which is considered by the user to have sufficient image quality is used as a good label and the medical image that is considered by the user to have insufficient image quality is used as an inferior label, regardless of interpretation or diagnosis.

In the first variation of the procedure shown in FIG. 11, in step S45, the determining function 23 generates information on whether the image quality of the medical image of the interest target region generated in real time satisfies a predetermined condition, e.g., information on whether the image quality is good or inferior. To generate the information, the determining function 23 inputs in real time the medical image of the interest target region generated in real time into the trained model that is constructed in advance for each interest target region and that outputs whether the image quality of the medical image satisfies a predetermined condition based on the medical image. When the medical image of the interest target region generated in real time is good in image quality, the determining function 23 automatically determines the data collection time by causing the nuclear medical diagnostic apparatus 101 to terminate scanning (raw data collection).

The second variation of the procedure shown in FIG. 11 is applied when the medical image includes an interest target part that can determine information (image quality index) on the image quality of the medical image. Examples of the image quality index of this type of interest target parts include, as described above, the noise of the liver, the contrast of the accumulation portion of a predetermined size such as the 10 mm accumulation portion, the noise of the spine, and the noise of the muscle. In the second variation, in step S45, the determining function 23 specifies a body part of interest target from the medical image generated in real time by pattern matching or the like, sets an ROI for the specified body part (interest target part), and obtains an image quality index for the set ROI. Then, the determining function 23 determines that the image quality of the interest target part generated in real time is good when the obtained image quality index is greater than or equal to the threshold value, and causes the nuclear medical diagnostic apparatus 101 to terminate scanning (raw data collection), thereby determining data collecting time automatically.

Figure 12:
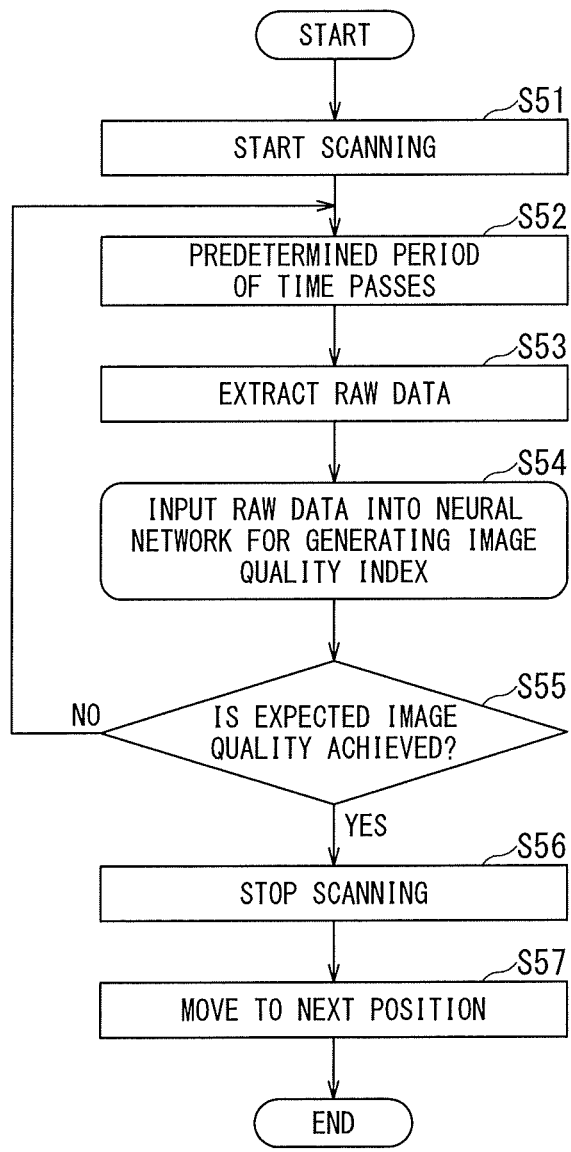
FIG. 12 is a flowchart showing an example of a procedure for obtaining a relationship between a collection time and a parameter value related to image quality based on raw data acquired in real time during imaging and based on a trained neural network for generating an image quality index.

FIG. 12 is a flowchart showing an example of a procedure for obtaining a relationship between a collection time and a parameter value related to image quality based on raw data acquired in real time during imaging and based on a trained neural network for generating an image quality index. The procedure shown in FIG. 12 is also performed concurrently with steps S12 and S13 in FIG. 6 or steps S32 and S33 in FIG. 10.

In the nuclear medical diagnostic apparatus 101, scanning is started (step S51), and when a predetermined period has passed (step S52), the acquisition function 22 acquires raw data up to that point (step S53).

Next, the determining function 23 acquires the parameter value related to the image quality of the medical image on the assumption that the medical image is generated based on the raw data at that point (step S54), by inputting the acquired raw data to a neural network for generating the image quality index that outputs a parameter value (image quality index) related to image quality based on the raw data and is constructed in advance (step S54).

Then, the determining function 23 determines whether the parameter value related to the image quality necessary for obtaining the desired lesion extraction accuracy with the desired lesion size has been reached (step S55). Since the procedure of steps S55-57 is the same as the procedure of steps S45-47 of FIG. 11, description thereof is omitted.

According to the above procedure, the parameter value related to the image quality can be obtained from the raw data acquired in real time during imaging, and the data collection time can be automatically determined.

Next, a variation example of the procedure shown in FIG. 12 will be described. In this variation, in step S54, the determining function 23 inputs the obtained raw data to the neural network for generating the image quality index that outputs the parameter value (image quality index) related to the image quality based on inputted raw data and that is constructed in advance, whereby the determining function 23 acquires the parameter value related to the image quality of the interest target region of the medical image on the assumption that the medical image is generated based on the inputted raw data. The determining function 23 then automatically determines the data collection time by causing the nuclear medical diagnostic apparatus 101 to end the scan (raw data collection) based on the parameter value. In this variation example, as in the first and the second variations for the procedure shown in FIG. 11, the determining function 23 causes the nuclear medical diagnostic apparatus 101 to terminate scanning (raw data collection) when the image quality of the interest target region is good, while the determining function 23 causes the nuclear medical diagnostic apparatus 101 to continue scanning (raw data collection) when the image quality of the interest target region is inferior.

In the variation example of the procedure shown in FIG. 12, in step S54, the determining function 23 inputs the raw data acquired in real time to the trained model that outputs information on the image quality of the medical image based on the raw data, thereby generating the information (image quality index) related to the image quality of the interest target region of the medical image corresponding to the raw data acquired in real time. When the image quality index of the interest target region generated in real time is equal to or higher than the threshold value, the determining function 23 determines that the image quality of the interest target region generated in real time is good, and determines the data collection time automatically by causing the nuclear medical diagnostic apparatus 101 to terminate scanning (raw data collection).

Figure 13:
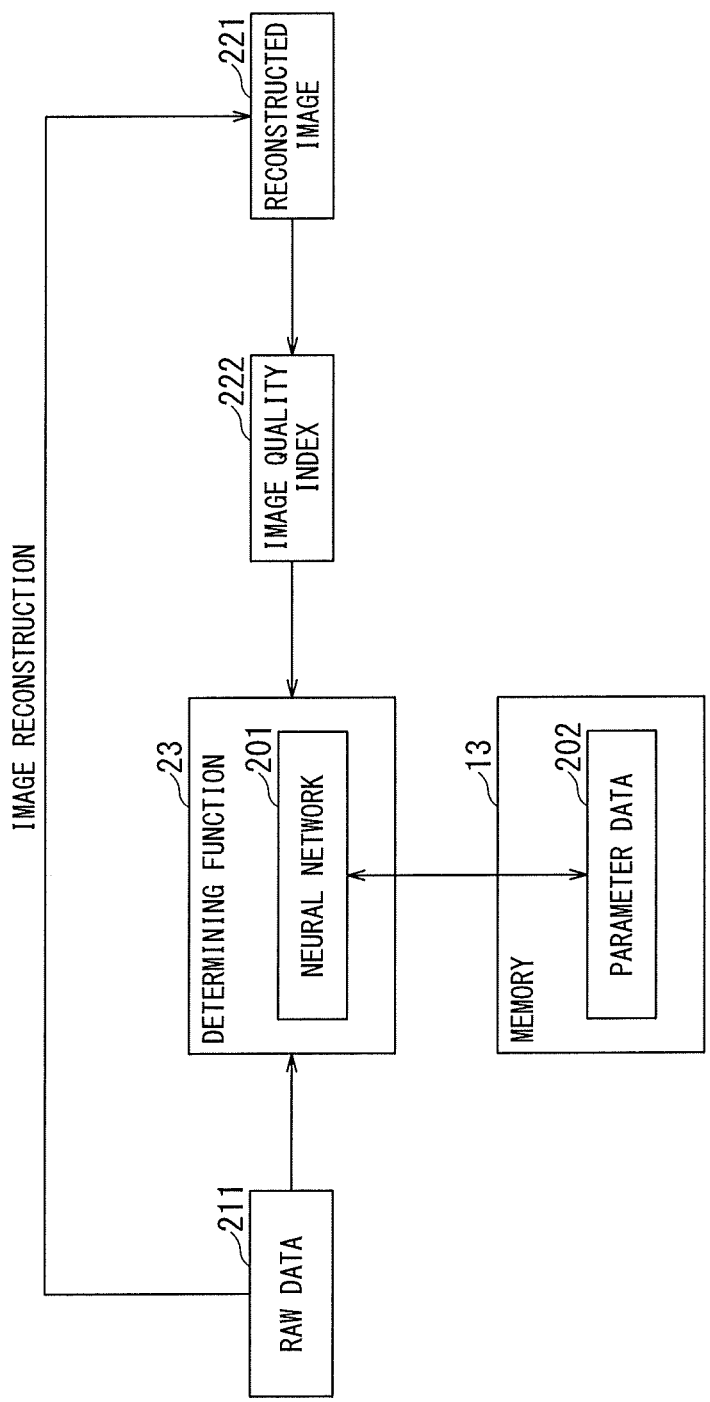
FIG. 13 is an explanatory diagram showing an example of a data flow during training of a determining function according to a variation of the procedure shown in FIG. 12.

FIG. 13 is an explanatory diagram showing an example of a data flow during training of the determining function 23 according to a variation of the procedure shown in FIG. 12.

In the variation of the procedure shown in FIG. 12, the determining function 23 performs training using the raw data 211 as training data (for input) and the image quality index 222 of the interest target region of the reconstructed image 221 obtained by reconstructing the raw data 211 as training data (for the desired output, for label).

Specifically, every time a set of the raw data 211 and the image quality index 222 is input, the determining function 23 updates the parameter data 202 and is trained such that the result of processing the raw data 211 by the neural network 201 approaches the image quality index 222. When the change rate of the parameter data 202 converges within a threshold value, it is determined that training is finished.

Hereinafter, the trained parameter data 202 is particularly referred to as trained parameter data 202a.

As described above, various methods are known for calculating the image quality index 222 of the interest target region of the reconstructed image 221, such as a method using noise of the liver, and any of these methods may be applied.

Figure 14:
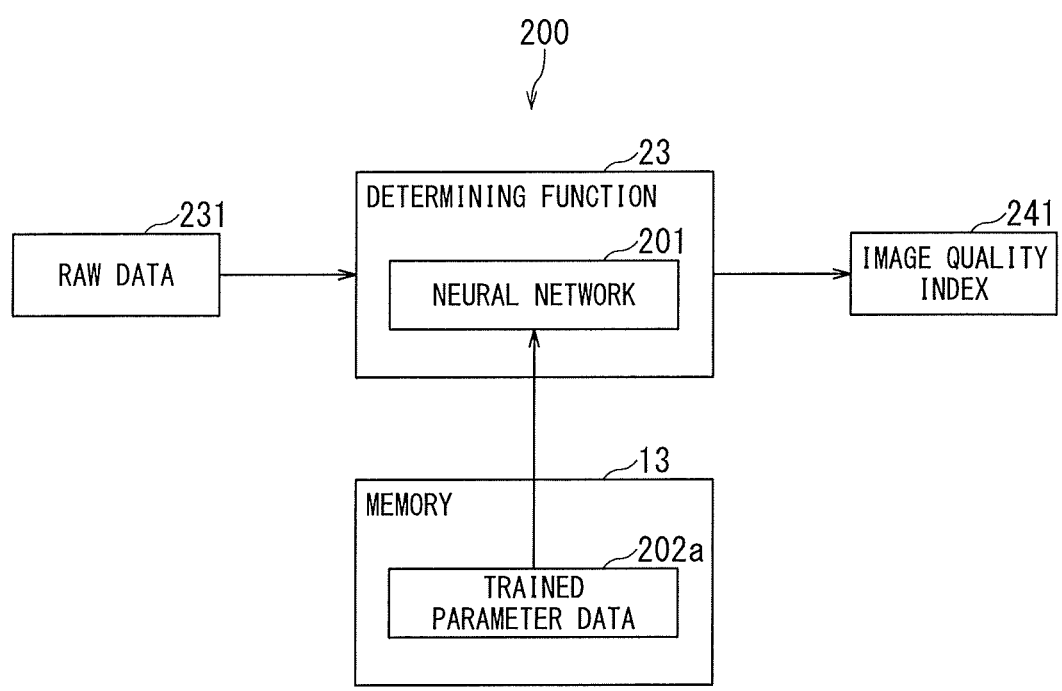
FIG. 14 is an explanatory diagram showing an example of a data flow during operation of the determining function according to a variation of the procedure shown in FIG. 12.

FIG. 14 is an explanatory diagram showing an example of a data flow during operation of the determining function 23 according to the variation of the procedure shown in FIG. 12. In the operation phase, the determining function 23 receives the raw data 231 acquired in real time, and generates by using the trained model 200 an image quality index of the interest target region of the medical image assuming that the medical image is generated based on the inputted raw data.

The neural network 201 and the learned parameter data 202a constitute the trained model 200. The trained model 200 may be constructed by an integrated circuit such as an application specific integrated circuit (ASIC) or a field programmable gate array (FPGA). Since the distribution of the configuration of the neural network 200 is the same as that of the neural network 31 of the processing function 24 according to the first embodiment, description thereof is omitted.

When association information between the parameter value related to the image quality and the number of counts (count value) of the raw data can be acquired in advance, the count value of the raw data may be used instead of the parameter value related to the image quality.

In this case, in step S54 of FIG. 12, the determining function 23 counts raw data. In step S55, the determining function 23 may determine whether the count value has reached a count value corresponding to a parameter value related to image quality necessary to obtain the desired lesion extraction accuracy with the desired lesion size. In the variation of the procedure shown in FIG. 12, in step S55, the determining function 23 determines whether this count value has reached a count value corresponding to a parameter value corresponding to image quality enough for diagnosis, for example.

Figure 15:
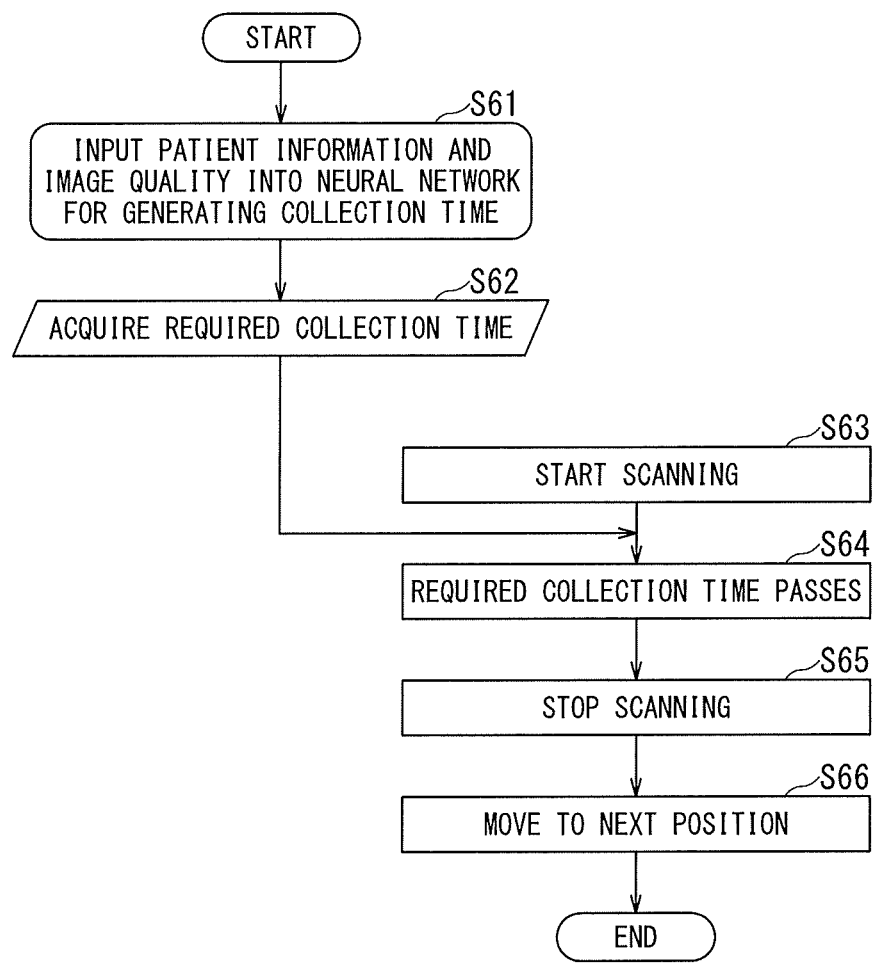
FIG. 15 is a flowchart showing an example of a procedure for obtaining a relationship between the collection time and the parameter value related to the image quality, based on information related to a physique of an object and a trained neural network for generating the collection time.

FIG. 15 is a flowchart showing an example of a procedure for obtaining a relationship between the collection time and the parameter value related to the image quality, based on information related to a physique of an object and a trained neural network for generating the collection time. Step S61 shown in FIG. 15 is executed in place of steps S12-13 in FIG. 6 or steps S32-33 in FIG. 10. This procedure may be executed in advance before the start of scanning.

The procedure shown in FIG. 15 starts when step S11 in FIG. 6 or step S31 in FIG. 10 is executed.

The determining function 23 inputs information on the physique of the object to be imaged and the parameter value related to the image quality necessary to obtain the desired lesion extraction correct answer rate with the desired lesion size to the neural network for generating the data collection time that is prepared in advance, and outputs the data collection time based on the information on the physique of the object and the parameter value related to the image quality of the medical image of the object, whereby the determining function 23 automatically determines the data collection time (step S61). The information on the determined data collection time is given to the nuclear medical diagnostic apparatus 101.

The nuclear medical diagnostic apparatus 101 starts scanning the object to be imaged (step S63), and when the data collection time determined in step S62 has elapsed (step S64), the scan is terminated (step S65), and the object is moved to the next imaging position (step S66).

According to the above procedure, the data collection time can be automatically determined based on the information on the physique of the object.

Third Embodiment

Figure 16:
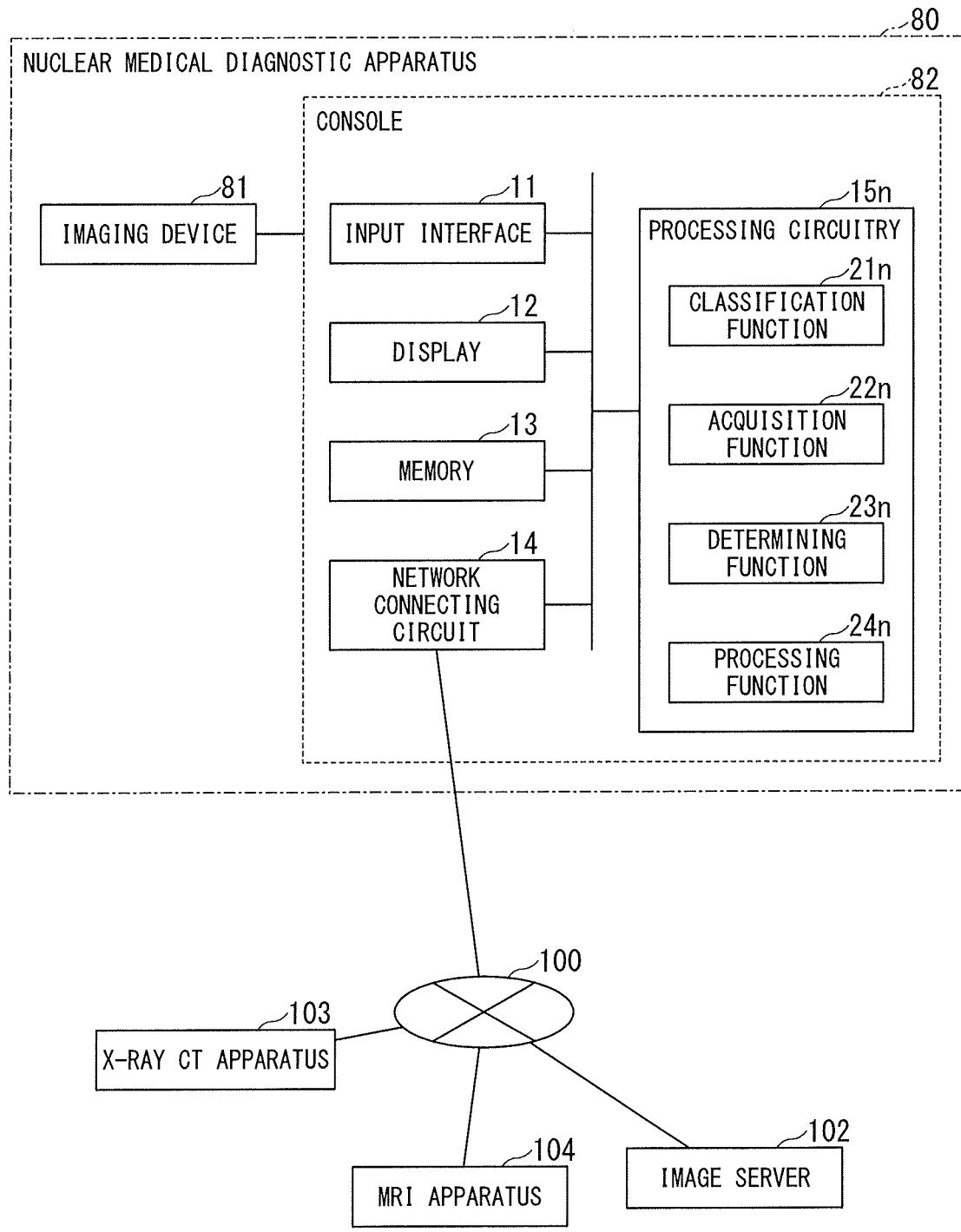
FIG. 16 is a block diagram showing an example of a nuclear medical diagnostic apparatus including a medical information processing apparatus according to the third embodiment.

FIG. 16 is a block diagram showing an example of the nuclear medical diagnostic apparatus 80 including a medical information processing apparatus according to the third embodiment.

The nuclear medical diagnostic apparatus 80 includes an imaging device 81 that captures a nuclear medicine image of the object, and a console 82 as an example of the medical information processing apparatus 10. The nuclear medical diagnostic apparatus 80 according to the third embodiment is different from the medical information processing apparatus 10 according to the first or the second embodiment in that the data related to the nuclear medicine image obtained by imaging the object by the nuclear medical diagnostic apparatus 80 itself is available. Since the other configurations and operations are not substantially different from the medical information processing apparatus 10 shown in FIG. 1, the same configurations are denoted by the same reference numerals and description thereof is omitted. Moreover, since the process before the operation of the trained model for lesion extraction is the same as the medical information processing apparatus 10 shown in the first and second embodiments, the description thereof is omitted.

The imaging device 81 has an imaging system including a gamma ray detector that detects the gamma rays emitted from the RI distributed in the object, and provides the data related to the nuclear medicine image of the object obtained by imaging to the console 82.

The classification function 21n and the determining function 23n of the processing circuitry 15n of the console 82 as the example of the medical information processing apparatus 10 are not substantially different from the classification function 21 and the determining function 23, respectively, and thus the description thereof is omitted.

The acquisition function 22n acquires the data related to the nuclear medicine image of the object from the imaging device 81. The processing function 24n determines the data collection time based on the data related to the nuclear medicine image of the object acquired from the imaging device 81.

Like the medical information processing apparatus 10 according to the first and the second embodiments, the nuclear medical diagnostic apparatus 80 according to the third embodiment can determine the imaging conditions of the medical image diagnostic apparatus according to the user desired value for the accuracy of the trained model.

According to at least one of the above-described embodiments, the imaging condition of the medical image diagnostic apparatus can be determined based on information on the image quality of the medical image.

The processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors is provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or variations as would fall within the scope and spirit of the inventions.

The invention claimed is:

1. A medical information processing apparatus comprising:
    processing circuitry configured to:
        acquire information on an accuracy of a trained model that outputs information on a lesion included in data related to a medical image based on inputted data related to the medical image,
        determine a data collection condition for the medical image in a medical image diagnostic apparatus based on the information on the accuracy,
        determine the data collection time for a nuclear medical diagnostic apparatus as the data collection condition,
        associate a size of the lesion, a parameter value related to an image quality, and the accuracy of the trained model by determining the accuracy of the trained model for each data group into which data related to medical images are classified into a plurality of groups according to the size of the lesion in the medical image and the parameter value related to the image quality of the medical image,
        acquire a set value of the size of the lesion and a desired value of the accuracy of the trained model, and
        determine the data collection time based on the relationship between data collection times and parameter values related to the image quality, the accuracy of the trained model determined for each data group, the set value of the size of the lesion, and the desired value of the accuracy of the trained model.

2. The medical information processing apparatus according to claim 1, wherein the trained model outputs information on a position of the lesion in the data related to the medical image based on the inputted data related to the medical image.

3. The medical information processing apparatus according to claim 1, wherein the processing circuitry is configured to determine an X-ray dose or a rotation speed of an X-ray tube of an X-ray CT apparatus as the acquisition condition.

4. The medical information processing apparatus according to claim 1, wherein the processing circuitry is configured to
generate a medical image from raw data in real time during a collection of the raw data by the nuclear medical diagnostic apparatus, and
determine the data collection time by terminating the data collection when a parameter value related to the image quality of the generated medical image is equal to or larger than a parameter value related to the image quality associated with the set value of the size of the lesion and the desired value of the accuracy of the trained model.

5. The medical information processing apparatus according to claim 1, wherein the processing circuitry is configured to
acquire raw data in real time during a collection of the raw data by the nuclear medical diagnostic apparatus,
generate a parameter value related to the image quality of the medical image corresponding to the raw data by inputting the acquired raw data to another trained model that outputs a parameter value related to an image quality of a medical image based on raw data, and
determine the data collection time by terminating the data collection when the generated parameter value related to the image quality is equal to or greater than a parameter value related to the image quality associated with the set value of the size of the lesion and the desired value of the accuracy of the trained model.

6. The medical information processing apparatus according to claim 1, wherein the processing circuitry is configured to determine the data collection time of an object to be imaged in the nuclear medical diagnostic apparatus by inputting information regarding a physique of the object to be imaged and a parameter value related to the image quality associated with the set value of the size of the lesion and the desired value of the accuracy of the trained model into another trained model that generates data collection time of a medical image based on information related to a physique of an object and a parameter value related to the image quality of the medical image of the object.

7. The medical information processing apparatus according to claim 1, wherein
the parameter value related to the image quality includes a raw data count value, and
the processing circuitry is configured to
calculate the raw data count value in real time during a collection of the raw data by the nuclear medical diagnostic apparatus, and
determine the data collection time by terminating the data collection when the calculated count value is equal to or greater than a count value associated with the set value of the size of the lesion and the desired value of the accuracy of the trained model.

8. A medical information processing apparatus comprising:
processing circuitry is configured to:
acquire information on image quality of an interest target region in data related to a nuclear medicine image based on inputted data related to the nuclear medicine image that is currently collected by a nuclear medical diagnostic apparatus, and
determine a data collection time of data currently being collected by the nuclear medical diagnostic apparatus based on the information on the image quality of the interest target region,
generate a medical image of the interest target region from raw data in real time during a collection of the raw data by the nuclear medical diagnostic apparatus,
generate information on whether an image quality of the medical image of the interest target region generated in real time satisfies a predetermined condition by inputting the medical image of the interest target region generated in real time to a trained model that outputs whether an image quality of a medical image satisfies the predetermined condition based on the medical image, and
determine the data collection time by terminating data collection when the image quality of the medical image of the interest target region generated in real time satisfies the predetermined condition.

9. A medical information processing apparatus comprising:
processing circuitry is configured to:
acquire information on image quality of an interest target region in data related to a nuclear medicine image based on inputted data related to the nuclear medicine image that is currently collected by a nuclear medical diagnostic apparatus, and
determine a data collection time of data currently being collected by the nuclear medical diagnostic apparatus based on the information on the image quality of the interest target region,
generate a medical image from raw data in real time during a collection of the raw data by the nuclear medical diagnostic apparatus, and
determine the data collection time by terminating data collection based on information on an image quality of the medical image of the interest target region generated in real time.

10. A medical information processing apparatus comprising:
processing circuitry is configured to:
acquire information on image quality of an interest target region in data related to a nuclear medicine image based on inputted data related to the nuclear medicine image that is currently collected by a nuclear medical diagnostic apparatus, and
determine a data collection time of data currently being collected by the nuclear medical diagnostic apparatus based on the information on the image quality of the interest target region,
acquire raw data in real time during a collection of the raw data by the nuclear medical diagnostic apparatus,
generate information on the image quality of the medical image of the interest target region corresponding to the raw data acquired in real time by inputting the raw data acquired in real time to a trained model that outputs information on an image quality of a medical image based on raw data, and
determine the data collection time by terminating the data collection based on the generated information on the image quality of the interest target region.

11. The medical information processing apparatus according to claim 8, wherein the processing circuitry is configured to calculate the raw data count value in real time during a collection of the raw data by the nuclear medical diagnostic apparatus, and determine the data collection time by terminating the data collection based on the calculated count value and based on information associating an image quality of the interest target region with a raw data count value.

* * * * *